United States Patent [19]

Willman et al.

[11] Patent Number: 4,645,758

[45] Date of Patent: Feb. 24, 1987

[54] URINARY INCONTINENCE AMELIORATING DIBENZ- B,E- -OXEPIN AND -THIEPIN DERIVATIVES, COMPOSITIONS, AND METHOD OF USE THEREFOR

[76] Inventors: Nils-Erik Willman, Alnarpsgatan 17, S-252 62 Helsingborg; Bengt C. H. Sjögren, Bygatan 39, S-260 40 Viken; Lennart G. Nordh, Färjemansgatan 12, S-252 40 Helsingborg; Gustav L. Persson, Ängelholm; Göran H. Sjöholm, Helsingborg, all of Sweden

[21] Appl. No.: 820,428

[22] Filed: Jan. 17, 1986

[30] Foreign Application Priority Data

Jan. 22, 1985 [SE] Sweden ............................ 8500273

[51] Int. Cl.[4] .................. A61K 31/335; A61K 31/36; A61K 31/38; C07D 337/12
[52] U.S. Cl. .................... 514/239; 514/253; 514/320; 514/324; 514/422; 514/431; 514/450; 544/145; 544/147; 544/375; 546/196; 546/202; 546/203; 548/525; 549/12; 549/354
[58] Field of Search ...................... 544/145, 147, 375; 546/196, 202, 203; 548/525; 549/12, 354; 514/239, 253, 320, 324, 422, 431, 450

[56] References Cited

U.S. PATENT DOCUMENTS 3,527,766  9/1970  Protiva et al. ................... 549/12
3,876,659  4/1975  Houlihan et al. ................ 549/12

FOREIGN PATENT DOCUMENTS 375532    4/1975  Sweden ............................ 549/12
1002234   8/1965  United Kingdom ................ 549/12

Primary Examiner—Henry H. Jiles
Assistant Examiner—J. G. Mullins
Attorney, Agent, or Firm—Scully, Scott, Murphy & Presser

[57] ABSTRACT

The invention concerns:

Novel dibenz/b,e/oxepin and dibenz/b,e/thiepin compounds having the general formula:

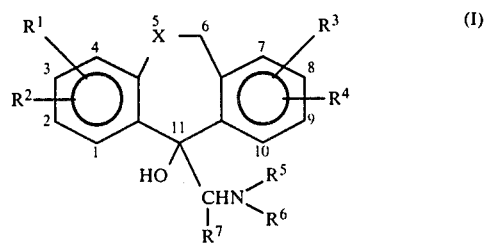

wherein
X is O or S,
$R^1$, $R^2$, $R^3$ and $R^4$ are the same or different and are each selected from the group consisting of hydrogen, lower alkyl, lower alkenyl, lower alkynyl, lower cycloalkyl, lower alkoxy, lower alkylthio, lower alkylsulphinyl, lower alkylsulponyl, halogen, trifluoromethyl, trifluoromethylthio, lower dialkylsulphonamido, nitro, hydroxy, cyano, carbamyl, carboxy, lower alkoxycarbonyl, amino, N-lower alkylamino, N,N-diloweralkylamino, lower acylamido, lower alkanesulfonamido and lower acyl and, when on adjacent carbon atoms at the positions 2 and 3 and/or 8 and 9, two of the substituents $R^1$ and $R^2$ or $R^3$ and $R^4$ taken together may form a methylenedioxy group;
$R^5$ and $R^6$ are the same or different and are selected from the group consisting of hydrogen, lower alkyl, lower alkenyl, lower alkynyl, lower cycloalkyl, aralkyl, lower hydroxyalkyl, lower aminoalkyl, lower alkylaminoalkyl, lower dialkylaminoalkyl, lower alkoxyalkyl and together with the nitrogen atom, $R^5$ and $R^6$ may form a 5- or 6- membered ring, such as pyrrolidine, piperidine, morpholine, piperazine, and N-lower alkyl or N-hydroxy lower alkyl substituted rings such as N-alkylpiperazine or N-hydroxyalkyl piperazine or the like,
$R^7$ is hydrogen or lower alkyl; optionally in the form of addition salts with pharmaceutically acceptable inorganic or organic acids and optionally in the form of essentially pure enantiomers.

The invention also includes compositions containing the novel compounds, processes for their preparation and a method of treatment therewith.

The compounds have pharmacological effects.

7 Claims, No Drawings

URINARY INCONTINENCE AMELIORATING DIBENZ- B,E- -OXEPIN AND -THIEPIN DERIVATIVES, COMPOSITIONS, AND METHOD OF USE THEREFOR

This invention relates to novel dibenz/b,e/oxepin and dibenz/b,e/thiepin derivatives having pharmacological properties. The invention is also concerned with pharmaceutical compositions containing said dibenz/b,e/oxepin or dibenz/b,e/thiepin derivatives and methods of treatment therewith.

BACKGROUND OF THE INVENTION

It is well known that urinary disorders i.e. the inability to control the urination is a great problem for many people. This problem can be solved in different ways. One way is to use surgical methods, which in some cases are well justified and give good results. For most people suffering from lighter forms of urinary disorders, however, the surgical methods are no realistic solution. Another way used by this category of people in order to solve this problem is to use drugs effecting the urinary bladder or urethra. The drugs which have been used till now have however not been sufficiently effective. Furthermore, these drugs have intolerable side effects.

OBJECTS OF THE INVENTION

One object of the invention is to provide new compounds having the general formula I as defined below.

A second object is to provide such types of compounds which can be employed in disorders, which are responsive to treatment with agents increasing the ability to control urination, i.e. the amelioration, alleviation, or elimination of urinary incontinence.

A third object of the invention is to provide processes for preparing the new compounds having the general formula I.

Another object of the invention is to provide a method of treating a living body suffering from a disorder which is responsive to treatment with agents which increase the ability to control urination, comprising the step of administering to said living body a compound having the general formula I, said compound being administered in an effective amount.

Yet another object of the invention is to provide compositions containing as an active ingredient one or more of the compounds having the general formula I, preferably together with a pharmaceutically acceptable carrier and, if desired, other pharmacologically active agents.

Other objects of the invention will become apparent to one skilled in the art and still other objects will become apparent hereinafter.

SUMMARY OF THE INVENTION

The compounds according to the present invention may be represented by the following general formula (I):

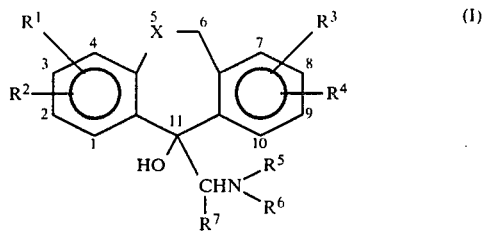

wherein
X is O or S;

R$^1$, R$^2$, R$^3$ and R$_4$ are the same or different and are each selected from the group consisting of hydrogen, lower alkyl, lower alkenyl, lower alkynyl, lower cycloalkyl, lower alkoxy, lower alkylthio, lower alkylsulphinyl, lower alkylsulphonyl, halogen, trifluoromethyl, trifluoromethylthio, lower dialkylsulphonamido, nitro, hydroxy, cyano, carbamyl, carboxy, lower alkoxycarbonyl, amino, N-lower alkylamino, N,N-dilower alkylamino, lower acylamido, lower alkanesulfonamido and lower acyl; and, when on adjacent carbon atoms at the positions 2 and 3 and/or 8 and 9, two of the substituents R$^1$ and R$^2$ or R$^3$ and R$^4$ taken together may form a methylenedioxy group;

R$^5$ and R$^6$ are the same or different and are selected from the group consisting of hydrogen, lower alkyl, lower alkenyl, lower alkynyl, lower cycloalkyl, aralkyl, lower hydroxyalkyl, lower aminoalkyl, lower alkylaminoalkyl, lower dialkylaminoalkyl, lower alkoxyalkyl and together with the nitrogen atom, R$^5$ and R$^6$ may form a 5- or 6-membered ring such as pyrrolidine, piperidine, morpholine, piperazine and N-lower-alkyl or N-hydroxy lower-alkyl substituted rings such as N-alkylpiperazine or N-hydroxyalkylpiperazine or the like, R$^7$ is H or lower alkyl, The general formula I includes the enantiomeric and racemic forms. The compounds of the present invention which contain salt-forming basic nitrogen atoms may also be in the form of addition salts with pharmaceutically acceptable inorganic or organic acids, the salts thus formed being such as the hydrochlorides, hydrobromides, phosphates, nitrates, sulphates, hydrogenoxalates, oxalates, succinates, tartrates, methanesulphonates and ethanedisulphonates.

In this disclosure the expression "lower" means that the group referred to contains one to four carbon atoms, inclusive. Thus, lower alkyl, lower alkenyl, lower alkynyl, lower alkoxy and lower cycloalkyl include for instance: methyl, ethyl, propyl, iso-propyl, butyl, secondary butyl, iso-butyl, tertiary butyl, vinyl, iso-propenyl, 1-propenyl, allyl, ethynyl, 1-propynyl, 2-propynyl, methoxy, ethoxy, propoxy, isopropoxy, butoxy, isobutoxy, secondary butoxy, tertiary butoxy, cyclopropyl and cyklobutyl.

With regard to the substituents R$^1$, R$^2$, R$^3$ and R$^4$ it is preferred that these substituents are hydrogen, lower alkyl, lower alkoxy, hydroxy, halogen, trifluoromethyl, cyano, carboxy, lower alkoxycarbonyl, amino, lower alkylamino, N,N-dilower alkylamino, lower acylamido, lower alkanesulfonamido. Mono- and disubstitution is preferred.

If selected from halogen atoms it is preferred that R$^1$, R$^2$, R$^3$ and R$^4$ are selected from the group consisting of fluoro, chloro and bromo. Especially preferred groups $R^1$, $R^2$, $R^3$ and $R^4$ are hydrogen, methyl, methoxy, hydroxy, chloro, fluoro, bromo, trifluoromethyl, cyano, carboxy, methoxycarbonyl, amino, methylamino, dimethylamino, formamido, acetamido, methanesulfonamido, trifluormethanesulfonamid.

The groups $R^5$ and $R^6$ are preferably selected from the group consisting of hydrogen, methyl, ethyl and hydroxyethyl.

The group $R^7$ is preferably hydrogen and methyl.

The following compounds are preferred:

2-chloro-11-dimethylaminomethyl-6,11-dihydrodibenz(b,e)oxepin-11-ol
9-chloro-11-dimethylaminomethyl-6,11-dihydrodibenz(b,e)oxepin-11-ol
2,9-dichloro-11-dimethylaminomethyl-6,11-dihydrodibenz(b,e)oxepin-11-ol
9-chloro-11-methylaminomethyl-6,11-dihydrodibenz(b,e)thiepin-11-ol
8-chloro-11-dimethylaminomethyl-6,11-dihydrodibenz(b,e)oxepin-11-ol
8-fluoro-11-methylaminomethyl-6,11-dihydrodibenz(b,e)oxepin-11-ol
9-fluoro-11-dimethylaminomethyl-6,11-dihydrodibenz(b,e)oxepin-11-ol
8-chloro-11-methylaminomethyl-6,11-dihydrodibenz(b,e)oxepin-11-ol
9-chloro-11-methylaminomethyl-6,11-dihydrodibenz(b,e)oxepin-11-ol
4-chloro-11-dimethylaminomethyl-6,11-dihydrodibenz(b,e)oxepin-11-ol
8-chloro-11-dimethylaminomethyl-6,11-dihydrodibenz(b,e)oxepin-11-ol
9-chloro-11-dimethylaminomethyl-6,11-dihydrodibenz(b,e)oxepin-11-ol
8-chloro-11-(2-hydroxyethyl)aminomethyl-6,11-dihydrodibenz(b,e)oxepin-11-ol
9-chloro-11-(2-hydroxyethyl)aminomethyl-6,11-dihydrodibenz(b,e)oxepin-11-ol
9-cyano-11-methylaminomethyl-6,11-dihydrodibenz(b,e)oxepin-11-ol
8-cyano-11-(2-hydroxyethyl)aminomethyl-6,11-dihydrodibenz(b,e)oxepin-11-ol
9-trifluoromethyl-11-methylaminomethyl-6,11-dihydrodibenz(b,e)oxepin-11-ol
7,8-dihydroxy-11-methylaminomethyl-6,11-dihydrodibenz(b,e)oxepin-11-ol
2-chloro-11-(1-amino)ethyl-6,11-dihydrodibenz(b,e)oxepin-11-ol
8-chloro-11-(1-amino)ethyl-6,11-dihydrodibenz(b,e)oxepin-11-ol
9-chloro-11-(1-amino)ethyl-6,11-dihydrodibenz(b,e)oxepin-11-ol
8-fluoro-11-(1-methylamino)ethyl-6,11-dihydrodibenz(b,e)oxepin-11-ol If desired the above compounds may also be in the form of salt with pharmaceutically acceptable organic or inorganic acids.

METHODS OF PREPARATION

The compounds having the general formula I may be prepared by conventional methods, and especially according to the following methods 1–8.

Method 1

A compound of the general formula II

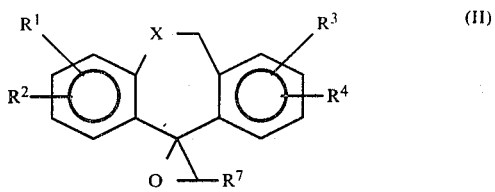

wherein X, $R^1$, $R^2$, $R^3$, $R^4$ and $R^7$ are as previously defined; is reacted with an amine having the general formula wherein $HNR^5R^6$, wherein $R^5$ and $R^6$ are as previously defined; to form a compound of the general formula I. (Method 1 above is illustrated in Example 1.)

Method 2

A compound of the general formula III,

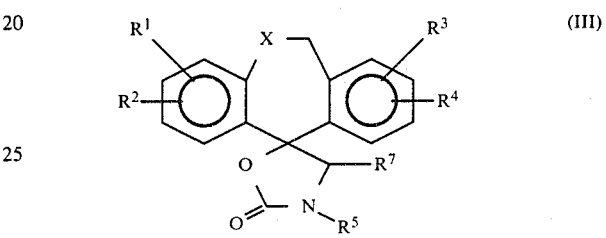

wherein X, $R^1$, $R^2$, $R^3$, $R^4$, $R^5$ and $R^7$ are as previously defined, is hydrolysed or reduced to a compound of the general formula I, wherein $R^6$ is hydrogen or methyl (Method 2 above is further illustrated in Examples 2 and 3.)

Method 3

A compound having the general formula IV,

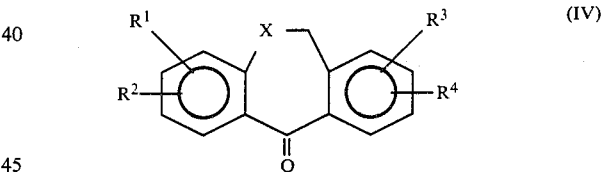

wherein X, $R^1$, $R^2$, $R^3$ and $R^4$ are as previously defined; is treated with a reactive amine wherein $LiCH_2NR^5R^6$ wherein $R^5$ or $R^6$ are lower alkyl or form a saturated ring system, to form a compound having the general formula I, wherein $R^7$ is hydrogen.

(Method 3 above is further illustrated in Example 4.)

Method 4

A compound of the general formula,

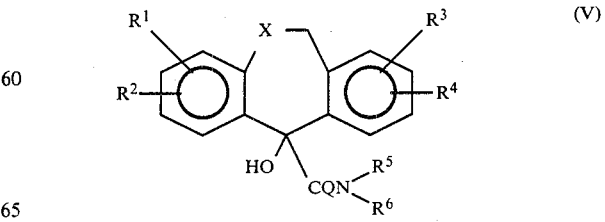

wherein X, $R^1$, $R^2$, $R^3$, $R^4$, $R^5$ and $R^6$ are as previously defined, and Q is oxygen or sulphur, is reduced to a compound of the general formula I, wherein $R^7$ is hydrogen.

(Method 4 above is further illustrated in Example 5.)

Method 5

A compound of the general formula,

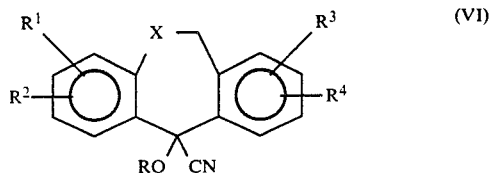

wherein X, $R^1$, $R^2$, $R^3$, and $R^4$ are as previously defined and R is hydrogen or trimethylsilyl; is reduced to a compound of the general formula I, wherein $R^5$, $R^6$ and $R^7$ are hydrogen.

(Method 5 above is further illustrated in Example 6.)

Method 6

A compound of the general formula I wherein, $R^1$, $R^2$, $R^3$ or $R^4$ is alkylthio, none of the substituents $R^5$, $R^6$ is hydrogen and $R^7$ is as previously defined, is oxidized selectively to convert $R^1$, $R^2$, $R^3$ or $R^4$ to an alkylsulphinyl group or alkylsulphonyl group as illustrated in Example 7.

Method 7

A compound of the general formula VII

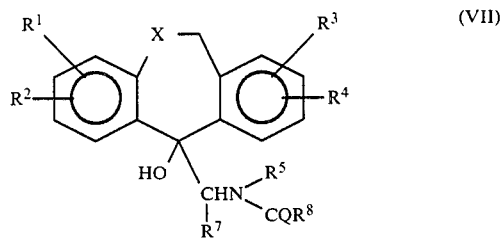

X, $R^1$, $R^2$, $R^3$, $R^4$, $R^5$ and $R^7$ are as previously defined and wherein Q is oxygen or sulphur or alkylsubstituted nitrogen and $R^8$ is the same as $R^6$ except for the fact that $R^8$ does not include more than three carbon atoms, is reduced to a compound of the general formula I. (Method 7 above is illustrated further in Example 8.)

Method 8

A compound of the general formula VIII

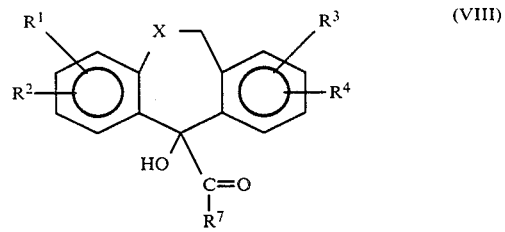

X, $R^1$, $R^2$, $R^3$, $R^4$ and $R^7$ are as previously defined, is reductively aminated with an amine $HNR^5R^6$ wherein $R^5$ and $R^6$ are as previously described to form a compound having the general formula I.

(Method 8 above is illustrated in Example 9.)

The following description is intended to give a more detailed illustration of the methods 1–8 corresponding to the processes a–h.

a. A process according to Method 1, characterized by reacting a compound of the general formula II with an amine $HNR^5R^6$ to form the product of the general formula I.

The reaction may be carried out by mixing the reagents or the reagents may be dissolved or suspended in an inert solvent such as an alcohol, e.g. ethanol, water, dimethyl sulphoxide, acetonitrile, etc. Mixtures of more than one solvent may be employed.

The reaction is preferably carried out between 20°–150° C., preferably between 40° and 130° C. The reaction may, if necessary, be carried out under pressure.

The resulting product may be isolated by conventional procedures.

The starting material of the formula II may be prepared from compounds of the general formula IV by methods described in reference (1). The crude spiroepoxides II are preferably directly reacted with amines.

b. A process according to Method 2 characterized by transforming compounds of the general formula III to compounds of the general formula I, wherein $R^6$ and $R^7$ are hydrogen or lower alkyl, by hydrolysis or reduction.

Alkaline hydrolysis of compounds of the general formula III is suitably carried out at a temperature in the range from 30° C. to 120° C., preferably between 70° C. and 110° C. and preferably in the presence of an inert organic solvent readily miscible with water, particularly a lower alcohol, e.g., ethanol.

Reduction of compounds of formula III is preferably carried out at a temperature in the range from 0° C. to 70° C. in the presence of an inert organic solvent, particularly ether or THF (tetrahydrofuran). Among various known reducing agents lithium aluminium hydride is preferred.

The starting material III may be prepared from compounds of the general formula IV by the method described in reference (2) or by cyclizising a compound of formula I, in which at least one of $R^5$ or $R^6$ is hydrogen with reactive derivatives of carbonic acid, e.g., phosgene or 1,1'-dicarbonyldiimidazole.

c. A process according to Method 3, characterized by reacting a reactive derivative of N-methylsubstituted tertiary amine with a compound of the general formula IV. The reaction may be carried out in an excess of the same amine or in an inert solvent medium at −70° C. or below.

The reactive derivative of the amine may be $LiCH_2NR^5R^6$, wherein $R^5$ and $R^6$ are lower alkyl groups or form a saturated ring system.

The reactive derivatives can be prepared according to the method described in reference (3) or from (n-$C_4H_9)_3SnCH_2NR^5R^6$ described in reference (4).

The starting amines $CH_3NR^5R^6$ are known compounds. Compounds having the general formula IV are known compounds or can be prepared by conventional methods as described in reference (5).

d. A process according to Method 4 characterized by reducing a tertiary amide V (Q=O) or tertiary thioamide V (Q=S) with a reducing agent to a compound of the general formula I, wherein $R^7$ is hydrogen. Amides V can be reduced to a compound of the general formula I, by using conventional reducing agents including LiAlH$_4$, BF$_3$-THF, NaBH$_4$-CoCl$_2$ etc. Thioamides can also be reduced with hydrogen and Raney-nickel.

The process may be carried out in an inert organic solvent compatible with the reducing agent.

The process may be performed at a temperature between 20° C. and 100° C.

The starting material of the general formula V may be prepared from compounds of the general formula IV by using methods described in reference (6).

e. A process according to Method 5 characterized by reduction of a nitrile VI with a reducing agent to a compound of the general formula I. The nitrile VI may be reduced by using a conventional reducing agent such as LiAlH$_4$, BH$_3$-THF, NaBH$_4$-Co etc. or by catalytic hydrogenation.

The process may be carried out in an inert solvent compatible with the reducing agent, e.g. hydrocarbons, ethers, alcohols, carboxylic acids. Mixtures of more than one solvent may also be employed.

The process may be performed at a temperature between 20° C. and 100° C.

The starting material VI may be prepared from compounds of the general formula IV by using general methods as described in reference (7).

f. A process according to Method 6, characterized by oxidizing a compound of the general formula I wherein $R^1$, $R^2$, $R^3$ or $R^4$ is an alkylthio group, none of the substituents $R^5$ or $R^6$ is hydrogen; and $R^7$ is as previously defined; selectively to a compound of the general formula I wherein $R^1$, $R^2$, $R^3$ or $R^4$ is alkylsulfinyl or alkylsulfonyl group.

This process is carried out by using known methods as described in references (8) and (9).

The process may be carried out at a temperature between 0° C. and 50° C., preferably between 10° C. and 35° C.

The process may be carried out in an inert solvent medium compatible with the oxidizing agent such as a carboxylic acid, e.g. trifluoroacetic acid, an alcohol, e.g. methanol or water. Mixtures of one or more solvents may be employed.

g. A process according to method 7 characterized by reducing a compound of the general formula VII with a reducing agent to a compound of the general formula I. Amides VII can be reduced by conventional reducing agents including LiAlH$_4$, BF$_3$.THF, NaBH$_4$.CoCl$_2$, etc. Thio amides may also be reduced with hydrogen and Raney-nickel.

The process may be carried out in an inert organic solvent compatible with the reducing agent.

The process may be performed at ambient temperatures, normally temperatures of 20° C.–100° C., are suitable.

The starting material of the general formula VII may be prepared by N-acylating compounds I wherein $R^6$=H with a reactive derivative of the carboxylic acid, $R^8$ COOH.

h. A process according to Method 8, characterized by reducing a compound of the general formula VIII in the presence of ammonia, or a primary. or secondary amine, HN $R^5R^6$.

The process of reductive alkylation of an amine consists in the addition of an amine to a carbonyl compound and reduction of the addition compound or its dehydrated product.

The reaction may be conducted conveniently in either high or low-pressure equipment. Raney nickel, platinum or palladium catalysts may be used.

The process may be carried out in an inert organic solvent such as alcohol, e.g., ethanol.

The process may be carried out at a pressure of 1 to 120 atm and at a temperature between 20° and 80° C.

The starting materials VIII may be prepared from compounds of the general formula IV by using methods described in references (11,12).

The racemic compounds of the general formula I may be resolved using known methods, such as various resolving acids, by crystallization of resolving acid salts of compounds of the general formula I in any of the suitable conventional inert organic solvents and preferably at a temperature from the boiling point of the solvent or mixture of solvents to −20° C.

The preferred solvents are ethanol, 1-propanol, 2-propanol and acetone. Water and mixtures of solvents may also be employed.

All the above processes, a-h, may optionally be carried out in the presence of a catalyst known to be useful in said process.

It is also possible in a manner known per se to prepare compounds having the general formula I above from other compounds within the definition of said general formula.

As examples of such transformations the following may be mentioned: Free hydroxy groups are, e.g., obtained by removal of acyl groups from carboxylic esters or by removal of lower alkyl groups from lower alkoxy groups. Free amino groups are, e.g., obtained by removal of acyl groups from carboxamides or by reduction of nitro groups. Lower alkylsulphinyl and lower alkylsulphonyl groups are, e.g., obtained by oxidation of methylthio groups. Lower alkoxycarbonyl groups are, e.g., obtained by esterification of carboxylic acids. On the other hand, free hydroxy groups can be esterified and etherified, primary and secondary amines acylated to amides, and amides can be reduced to corresponding amines.

In synthesizing compounds having the general formula I by any of the methods mentioned above, each group of the starting materials involved must be compatible with the process in question or, if necessary, protected during one or more reaction steps and then converted to the desired group. Pertinent examples of groups that may be protected are hydroxy- and primary and secondary amino groups.

The compounds of the invention are generally characterized by the pharmacological activity hereinbefore stated, making them useful in counteracting certain physiological abnormalities in a living human body. Effective quantities of a pharmacologically active compound of the invention may be administered to a living animal body in any one of various ways, e.g., orally as in capsules or tablets, parenterally in the form of sterile solutions, suspensions, and by pellet implantation. Among routes of parenteral administration are intravenously, subcutaneously, intramuscularly, intraperitoneally, intraarticularly, and intradermally. Other modes of administration are vaginally, rectally, and topically as, e.g., in the form of ointments, suppositories, and powders.

Pharmaceutical formulations are usually prepared from a predetermined quantity of one or more of the compounds of the invention. Such formulations may take the form of powder, syrups, suppositories, ointments, solutions, pills, capsules, pellets or tablets, suspensions, emulsions, oil solutions, etc. with or without, but preferably with, any one of a large variety of pharmaceutically acceptable vehicles or carriers. When in a mixture with a pharmaceutical vehicle or carrier, the active ingredient usually comprises from about 0.01 to about 75%, normally from about 0.05 to about 15%, by weight of the composition. Carriers such as starch, sugar, talc, commonly used synthetic and natural gums, water, and the like, may be used in such formulations. Binders such as polyvinylpyrrolidone, and lubricants such as sodium stearate, may be used to form tablets. Disintegrating agents such as sodium carbonate may also be included in tablets.

Although relatively small quantities of the active materials of the invention, even as low as 5.0 milligrams, may be used in cases of administration to subjects having a relatively low body weight, unit dosages are preferably 5 milligrams or above and preferably 25, 50, or 100 milligrams, or even higher, depending of course upon the subject treated and the particular result desired, as will be apparent to one skilled in the art. Broader ranges appear to be 1 to 1000 milligrams per unit dose.

The present compounds may be administered in a quantity of 1 to 1000 milligrams, preferred ranges being 5–250 milligrams per day per subject or patient, divided in 1 to 4 or more doses, over a suitable period and depending upon the subject and the type of subject being treated.

DETAILED DESCRIPTION OF THE INVENTION

The following examples are intended to illustrate but not to limit the scope of the invention, although the compounds named are of particular interest for our intended purposes. These compounds have been designated by underlined numbers in the examples where their preparations are described and where their systematic names are given. The compounds are later on referred to by a number code, a:b, where "a" means the number of the example, wherein the preparation of the compound in question is described, and "b" refers to the order of the compounds prepared according to that example. Thus, compound 1:2 means the second compound prepared according to Example 1.

The structures of the compounds found in Examples 1-9 are confirmed by NMR and elementary analysis. The NMR data are recorded using a 60 MHz instrument (Perkin-Elmer R 12). Melting points are determined with a Mettler FP-apparatus and optical rotation is measured with a Perkin-Elmer 241 polarimeter.

EXAMPLE 1

Spiro(2-chloro-6,11-dihydrodibenz(b,e)oxepin-11,2'-oxirane) (2.24 g, 0.01 mole) together with 0.2 ml of water and methylamine (15 ml) is heated in a pressure vessel at 110° C. over night. After cooling the excess of the amine is evaporated. The residue is poured into 100 ml of water and extracted with ether. The ether layer is extracted with 0.5M hydrochloric acid and water. The aqueous layer is washed with ether, made alkaline with 2M sodium hydroxide and extracted with ether. The ether layer is washed with water and dried over anhydrous sodium sulphate. The desired product is isolated as the hydrochloride and recrystallized from ethanol-ether. 2-chloro-11-methylaminomethyl-6,11-dihydrodibenz(b,e)oxepin-11-ol, hydrochloride. M.p. 226° C. (1).

In essentially the same manner the following compounds are obtained from the corresponding starting materials:

2. 11-aminomethyl-6,11-dihydrodibenz(b,e)oxepin-11-ol, m.p. 157° C.
3. 11-methylaminomethyl-6,11-dihydrodibenz(b,e)oxepin-11-ol, hydrochloride, m.p. 152° C.
4. 11-dimethylaminomethyl-6,11-dihydrodibenz(b,e)oxepin-11-ol, hydrochloride, m.p. 200° C.
5. 11-ethylaminomethyl-6,11-dihydrodibenz(b,e)oxepin-11-ol, hydrochloride, m.p. 181° C.
6. 11-diethylaminomethyl-6,11-dihydrodibenz(b,e)oxepin-11-ol, hydrochloride, m.p. 208° C.
7. 11-(2-hydroxyethyl)aminomethyl-6,11-dihydrodibenz(b,e)oxepin-11-ol, hydrochloride, m.p. 155° C.
8. 11-cyclopropylaminomethyl-6,11-dihydrodibenz(b,e)oxepin-11-ol, hydrochloride, m.p. 173° C.
9. 11-bis(2-hydroxyethyl)aminomethyl-6,11-dihydrodibenz(b,e)oxepin-11-ol, m.p. 121° C.
10. 11-piperidinomethyl-6,11-dihydrodibenz(b,e)oxepin-11-ol, m.p. 108° C.
11. 11-morpholinomethyl-6,11-dihydrodibenz(b,e)oxepin-11-ol, m.p. 120° C.
12. 11-/1-(3-hydroxypiperidyl)methyl/-6,11-dihydrodibenz(b,e)oxepin-11-ol, hydrochloride, m.p. 191° C.
13. 2-methyl-11-methylaminomethyl-6,11-dihydrodibenz(b,e)oxepin-11-ol, hydrochloride, m.p. 196° C.
14. 2-methoxy-11-methylaminomethyl-6,11-dihydrodibenz(b,e)oxepin-11-ol, hydrochloride, m.p. 205° C.
15. 2-chloro-11-methylaminomethyl-6,11-dihydrodibenz(b,e)oxepin-11-ol, hydrochloride, m.p. 221° C.
16. 2-bromo-11-methylaminomethyl-6,11-dihydrodibenz(b,e)oxepin-11-ol, hydrochloride, m.p. 226° C.
17. 2-fluoro-11-methylaminomethyl-6,11-dihydrodibenz(b,e)oxepin-11-ol, hydrochloride, m.p. 221° C.
18. 4-methoxy-11-methylaminomethyl-6,11-dihydrodibenz(b,e)oxepin-11-ol, hydrochloride, m.p. 219° C.
19. 2-methylthio-11-methylaminomethyl-6,11-dihydrodibenz(b,e)oxepin-11-ol, hydrochloride, m.p. 198° C.
20. 2-methylsulphinyl-11-methylaminomethyl-6,11-dihydrodibenz(b,e)oxepin-11-ol, hydrochloride, m.p. 223° C.
21. 2-methyl-11-dimethylaminomethyl-6,11-dihydrodibenz(b,e)oxepin-11-ol, hydrochloride, m.p. 237° C.
22. 2-methoxy-11-dimethylaminomethyl-6,11-dihydrodibenz(b,e)oxepin-11ol, hydrochloride, m.p. 205° C.
23. 2-chloro-11-dimethylaminomethyl-6,11-dihydrodibenz(b,e)oxepin-11-ol, hydrochloride, m.p. 246° C.
24. 2-bromo-11-dimethylaminomethyl-6,11-dihydrodibenz(b,e)oxepin-11-ol, hydrochloride, m.p. 238° C.
25. 2-fluoro-11-dimethylaminomethyl-6,11-dihydrodibenz(b,e)oxepin-11-ol, hydrochloride, m.p. 249° C.

26. 4-chloro-11-dimethylaminomethyl-6,11-dihydrodibenz(b,e)oxepin-11-ol, hydrochloride, m.p. 220° C.
27. 4-methoxy-11-dimethylaminomethyl-6,11-dihydrodibenz(b,e)oxepin-11-ol, hydrochloride, m.p. 230° C.
28. 9-chloro-11-dimethylaminomethyl-6,11-dihydrodibenz(b,e)oxepin-11-ol, hydrochloride, m.p. 255° C.
29. 2-trifluoromethyl-11-dimethylaminomethyl-6,11-dihydrodibenz(b,e)-oxepin-11-ol, hydrochloride, m.p. 205° C.
30. 2-methylthio-11-dimethylaminomethyl-6,11-dihydrodibenz(b,e)oxepin-11-ol, hydrochloride
31. 2-methylsulfinyl-11-dimeth.ylaminomethyl-6,11-dihydrodibenz(b,e)-oxepin-11-ol, hydrochloride
32. 3-methyl-11-dimethylaminomethyl-6,11-dihydrodibenz(b,e)oxepin-11-ol, hydrochloride, m.p. 204° C.
33. 2-cyano-11-dimeth.ylaminomethyl-6,11-dihydrodibenz(b,e)oxepin-11-ol,
34. 2-carbamyl-11-dimethylaminomethyl-6,11-dihydrodibenz(b,e)oxepin-11-ol, hydrochloride, m.p. 189° C.
35. 8-chloro-11-dimethylaminomethy.1-6,11-dihydrodibenz(b,e)oxepin-11-ol, hydrochloride, m.p. 222° C.
36. 8-chloro-11-methylaminomethyl-6,11-dihydrodibenz(b,e)oxepin-11-ol, hydrochloride, m.p. 184.5° C.
37. 2-chloro-11-aminomethyl-6,11-dihydrodibenz(b,e)oxepin-11-ol, hydrochloride, m.p. 212° C.
38. 8-chloro-11-(2-hydroxyethyl)aminomethyl-6,11-dihydrodibenz(b,e)-oxepin-11-ol, hydrochloride, m.p. 173° C.
39. 2,9-dichloro-11-dimethylaminomethyl-6,11-dihydrodibenz(b,e)oxepin-11-ol, hydrochloride, m.p. 257° C.
40. 2,9-dichloro-11-methylaminomethyl-6,11-dihydrodibenz(b,e)oxepin-11-ol, hydrochloride, m.p. 247° C.
41. 2,9-dichloro-11-(2-hydroxyethyl)aminomethyl-6,11-dihydrodibenz(b,e)oxepin-11-ol, hydrochloride, m.p. 224° C.
42. 2-methoxy-11-(2-hydroxyethyl)aminomethyl-6,11-dihydrodibenz(b,e)oxepin-11-ol, hydrochloride, m.p. 144° C.
43. 2-chloro-11-(2-hydroxyethyl)aminomethyl-6,11-dihydrodibenz(b,e)oxepin-11-ol, hydrochloride, m.p. 176° C.
44. 2-bromo-11-(2-hydroxyethyl)aminomethyl-6,11-dihydrodibenz(b,e)oxepin-11-ol, hydrochloride, m.p. 197° C.
45. 2-fluoro-11-(2-hydroxyethyl)aminomethyl-6,11-dihydrodibenz(b,e)oxepin-11-ol, hydrochloride, m.p. 179° C.
46. 2-methylthio-11-(2-hydroxyethyl)aminomethyl-6,11-dihydrodibenz(b,e)oxepin-11-ol, hydrochloride
47. 2-methylsulphinyl-11-(2-hydroxyethyl)aminomethyl-6,11-dihydrodibenz(b,e)oxepin-11-ol, hydrochloride
48. 2-chloro-11-diethy.laminomethyl-6,11-dihydrodibenz(b,e)oxepin-11-ol, hydrochloride, m.p. 227° C.
49. 2-chloro-11-ethylaminomethyl-6,11-dihydrodibenz(b,e)oxepin-11-ol, hydrochloride, m.p. 231° C.
50. 2-chloro-11-(N-methyl-N-(2-(methylamino)ethyl)aminomethyl-6,11-dihydrodibenz(b,e)oxepin-11-ol, hydrochloride, m.p. 220° C.
51. 11-methylaminomethyl-6,11-dihydrodibenz(b,e)thiepin-11-ol, hydrochloride, m.p. 182° C.
52. 2-chloro-11-dimethylaminomethyl-6,11-dihydrodibenz(b,e)thiepin-11-ol, hydrochloride, m.p. 255° C.
53. 2,4-dichloro-11-dimethylaminomethyl-6,11-dihydrodibenz(b,e)oxepin 11-ol, hydrochloride, m.p.221° C.
54. 2,4-dichloro-11-methylaminomethyl-6,11-dihydrodibenz(b,e)oxepin-11-ol, hydrochloride, m.p. 243° C.
55. 2,4-dichloro-11-(2-hydroxyethyl)aminomethyl-6,11-dihydrodibenz(b,e)oxepin-11-ol, hydrochloride, m.p. 179° C.
56. 4-chloro-11-methylaminomethyl-6,11-dihydrodibenz(b,e)thiepin-11-ol
57. 8-chloro-11-methylaminomethyl-6,11-dihydrodibenz(b,e)thiepin-11-ol
58. 9-chloro-11-methylaminomethyl-6,11-dihydrodibenz(b,e)thiepin-11-ol
59. 4-chloro-11-dimethylaminomethyl-6,11-dihydrodibenz(b,e)thiepin-11-ol
60. 8-chloro-11-dimethylaminomethyl-6,11-dihydrodibenz(b,e)thiepin-11-ol
61. 9-chloro-11-dimethylaminomethyl-6,11-dihydrodibenz(b,e)thiepin-11-ol
62. 4-chloro-11-(2-hydroxyethyl)aminomethyl-6,11-dihydrodibenz(b,e)thiepin-11-ol
63. 8-chloro-11-(2-hydroxyethyl)aminomethyl-6,11-dihydrodibenz(b,e)thiepin-11-ol
64. 9-chloro-11-(2-hydroxyethyl)aminomethyl-6,11-dihydrodibenz(b,e)thiepin-11-ol
65. 8-chloro-11-aminomethyl-6,11-dihydrodibenz(b,e)thiepin-11-ol
66. 9-chloro-11-aminomethyl-6,11-dihydrodibenz(b,e)thiepin-11-ol
67. 8-fluoro-11-methylaminomethyl-6,11-dihydrodibenz(b,e)oxepin-11-ol
68. 8-fluoro-11-(2-hydroxyethyl)aminomethyl-6,11-dihydrodibenz(b,e)oxepin-11-ol
69. 3-chloro-11-methylaminomethyl-6,11-dihydrodibenz(b,e)oxepin-11-ol
70. 4-chloro-11-methylaminomethyl-6,11-dihydrodibenz(b,e)oxepin-11-ol, hydrochloride, m.p. 95° C.
71. 7-chloro-11-methylaminomethyl-6,11-dihydrodibenz(b,e)oxepin-11-ol
72. 10-chloro-11-methylaminomethyl-6,11-dihydrodibenz(b,e)oxepin-11-ol
73. 3-chloro-11-dimethylaminomethyl-6,11-dihydrodibenz(b,e)oxepin-11-ol
74. 7-chloro-11-dimethylaminomethyl-6,11-dihydrodibenz(b,e)oxepin-11-ol
75. 10-chloro-11-dimethylaminomethyl-6,11-dihydrodibenz(b,e)oxepin-11-ol
76. 3-chloro-11-(2-hydroxyethyl)aminomethyl-6,11-dihydrodibenz(b,e)oxepin-11-ol
77. 4-chloro-11-(2-hydroxyethyl)aminomethyl-6,11-dihydrodibenz(b,e)oxepin-11-ol, hydrochloride, m.p. 92° C.
78. 7-chloro-11-(2-hydroxyethyl)aminomethyl-6,11-dihydrodibenz(b,e)oxepin-11-ol
79. 9-chloro-11-(2-hydroxyethyl)aminomethyl-6,11-dihydrodibenz(b,e)oxepin-11-ol hydrochloride, m.p. 193° C.

80. 10-chloro-11-(2-hydroxyethyl)aminomethyl-6,11-dihydrodibenz(b,e)oxepin-11-ol
81. 7-chloro-11-aminomethyl-6,11-dihydrodibenz(b,e)oxepin-11-ol
82. 8-chloro-11-aminomethyl-6,11-dihydrodibenz(b,e)-11ol, hydrochloride, m.p. 176° C.
83. 9-chloro-11-aminomethyl-6,11-dihydrodibenz(b,e)oxepin-11-ol, hydrochloride, m.p. 180° C.
84. 10-chloro-11-aminomethyl-6,11-dihydrodibenz(b,e)oxepin-11-ol
85. 7-fluoro-11-methylaminomethyl-6,11-dihydrodibenz(b,e)oxepin-11-ol
86. 7-fluoro-11-(2-hydroxyethyl)aminomethyl-6,11-dihydrodibenz(b,e)oxepin-11-ol
87. 9-fluoro-11-methylaminomethyl-6,11-dihydrodibenz(b,e)oxepin-11-ol
88. 9-fluoro-11-dimethylaminomethyl-6,11-dihydrodibenz(b,e)oxepin-11-ol
89. 9-fluoro-11-(2-hydroxyethyl)aminomethyl-6,11-dihydrodibenz(b,e)oxepin-11-ol
90. 4-chloro-11-aminomethyl-6,11-dihydrodibenz(b,e)oxepin-11-ol, hydrochloride, m.p. 201° C.
91. 4-fluoro-11-(2-hydroxyethyl)aminomethyl-6,11-dihydrodibenz(b,e)oxepin-11-ol
92. 4-fluoro-11-methylaminomethyl-6,11-dihydrodibenz(b,e)oxepin-11-ol
93. 4-hydroxy-11-methylaminomethyl-6,11-dihydrodibenz(b,e)oxepin-11-ol
94. 7-hydroxy-11-methylaminomethyl-6,11-dihydrodibenz(b,e)oxepin-11-ol
95. 8-hydroxy-11-methylaminomethyl-6,11-dihydrodibenz(b,e)oxepin-11-ol
96. 9-hydroxy-11-methylaminomethyl-6,11-dihydrodibenz(b,e)oxepin-11-ol
97. 9-hydroxy-11-dimethylaminomethyl-6,11-dihydrodibenz(b,e)oxepin-11-ol
98. 8-methoxy-11-aminomethyl-6,11-dihydrodibenz(b,e)oxepin-11-ol
99. 8-methoxy-11-methylaminomethyl-6,11-dihydrodibenz(b,e)oxepin-11-ol
100. 8-methoxy-11-dimethylaminomethyl-6,11-dihydrodibenz(b,e)oxepin-11-ol
101. 8-methoxy-11-(2-hydroxyethyl)aminomethyl-6,11-dihydrodibenz(b,e)oxepin-11-ol
102. 9-methoxy-11-methylaminomethyl-6,11-dihydrodibenz(b,e)oxepin-11-ol
103. 9-methoxy-11-dimethylaminomethyl-6,11-dihydrodibenz(b,e)oxepin-11-ol
104. 9-methoxy-11-(2-hydroxyethyl)aminomethyl-6,11-dihydrodibenz(b,e)oxepin-11-ol
105. 8-nitro-11-methylaminomethyl-6,11-dihydrodibenz(b,e)oxepin-11-ol
106. 8-nitro-11-dimethylaminomethyl-6,11-dihydrodibenz(b,e)oxepin-11-ol
107. 8-nitro-11-(2-hydroxyethyl)aminomethyl-6,11-dihydrodibenz(b,e)-oxepin-11-ol
108. 9-nitro-11-methylaminomethyl-6,11-dihydrodibenz(b,e)oxepin-11-ol
109. 9-nitro-11-dimethylaminomethyl-6,11-dihydrodibenz(b,e)oxepin-11-ol
110. 9-nitro-11-(2-hydroxyethyl)aminomethyl-6,11-dihydrodibenz(b,e)oxepin-11-ol
111. 8-amino-11-methylaminomethyl-6,11-dihydrodibenz(b,e)oxepin-11-ol
112. 8-amino-11-dimethylaminomethyl-6,11-dihydrodibenz(b,e)oxepin-11-ol
113. 8-amino-11-2-hydroxyethyl)aminomethyl-6,11-dihydrodibenz(b,e)oxepin-11-ol
114. 9-amino-11-methylaminomethyl-6,11-dihydrodibenz(b,e)oxepin-11-ol
115. 9-amino-11-dimethylaminometh.yl-6,11-dihydrodibenz(b,e)oxepin-11-ol
116. 9-amino-11-(2-hydroxyethyl)aminomethyl-6,11-dihydrodibenz(b,e)oxepin-11-ol
117. 9-methylamino-11-methylaminomethyl-6,11-dihydrodibenz(b,e)oxepin-11-ol
118. 9-methylamino-11-dimethylaminomethyl-6,11-dihydrodibenz(b,e)oxepin-11-ol
119. 9-methylamino-11-(2-hydroxyethyl)aminomethyl-6,11-dihydrodibenz(b,e)oxepin-11-ol
120. 8-formamido-11-methylaminomethyl-6,11-dihydrodibenz(b,e)oxepin-11-ol
121. 9-formamido-11-dimethylaminomethyl-6,11-dihydrodibenz(b,e)oxepin-11-ol
122. 8-acetamido-11-methylaminomethyl-6,11-dihydrodibenz(b,e)oxepin-11-ol
123. 9-acetamido-11-dimethylaminomethyl-6,11-dihydrodibenz(b,e)oxepin-11-ol
124. 8-methanesulfonamido-11-dimethylaminomethyl-6,11-dihydrodibenz(b,e)oxepin-11-ol
125. 9-methanesulfonamido-11-dimethylaminomethyl-6,11-dihydrodibenz(b,e)oxepin-11-ol
126. 9-methyl-11-methylaminomethyl-6,11-dihydrodibenz(b,e)oxepin-11-ol
127. 9-methyl-11-dimethylaminomethyl-6,11-dihydrodibenz(b,e)oxepin-11-ol
128. 9-methyl-11-(2-hydroxyethyl)aminomethyl-6,11-dihydrodibenz(b,e)oxepin-11-ol
129. 8-methyl-11-(2-hydroxyethyl)aminomethyl-6,11-dihydrodibenz(b,e)oxepin-11-ol
130. 4-methoxycarbonyl-11-aminomethyl-6,11-dihydrodibenz(b,e)oxepin-11-ol
131. 7-methoxycarbonyl-11-aminomethyl-6,11-dihydrodibenz(b,e)oxepin-11-ol
132. 8-methoxycarbonyl-11-aminomethyl-6,11-dihydrodibenz(b,e)oxepin-11-ol
133. 9-methoxycarbonyl-11-aminomethyl-6,11-dihydrodibenz(b,e)oxepin-11-ol
134. 10-methoxycarbonyl-11-aminomethyl-6,11-dihydrodibenz(b,e)oxepin-11-ol
135. 4-methoxycarbonyl-11-methylaminomethyl-6,11-dihydrodibenz(b,e)oxepin-11-ol
136. 7-methoxycarbonyl-11-methylaminomethyl-6,11-dihydrodibenz(b,e)oxepin-11-ol
137. 8-methoxycarbonyl-11-methylaminomethyl-6,11-dihydrodibenz(b,e)oxepin-11-ol
138. 9-methoxycarbonyl-11-methylaminomethyl-6,11-dihydrodibenz(b,e)oxepin-11-ol
139. 10-methoxycarbonyl-11-methylaminomethyl-6,11-dihydrodibenz(b,e)oxepin-11-ol
140. 4-methoxycarbonyl-11-dimethylaminomethyl-6,11-dihydrodibenz(b,e)oxepin-11-ol
141. 7-methoxycarbonyl-11-dimethylaminomethyl-6,11-dihydrodibenz(b,e)oxepin-11-ol
142. 8-methoxycarbonyl-11-dimethylaminomethyl-6,11-dihydrodibenz(b,e)oxepin-11-ol
143. 9-methoxycarbonyl-11-dimethylaminomethyl-6,11-dihydrodibenz(b,e)oxepin-11-ol
144. 10-methoxycarbonyl-11-dimethylaminomethyl-6,11-dihydrodibenz(b,e)oxepin-11-ol
145. 4-methoxycarbonyl-11-(2-hydroxyethyl)aminomethyl-6,11-dihydrodibenz(b,e)oxepin-11-ol
146. 7-methoxycarbonyl-11-(2-hydroxyethyl)aminomethyl-6,11-dihydrodibenz(b,e)oxepin-11-ol
147. 8-methoxycarbonyl-11-(2-hydroxyethyl)aminomethyl-6,11-dihydrodibenz(b,e)oxepin-11-ol 148. 9-methoxycarbonyl-11-(2-hydroxyethyl)aminomethyl-6,11-dihydrodibenz(b,e)oxepin-11-ol
149. 10-methoxycarbonyl-11-(2-hydroxyethyl)aminomethyl-6,11-dihydrodibenz(b,e)oxepin-11-ol
150. 4-cyano-11-aminomethyl-6,11-dihydrodibenz(b,e)oxepin-11-ol
151. 7-cyano-11-aminomethyl-6,11-dihydrodibenz(b,e)oxepin-11-ol
152. 8-cyano-11-aminomethyl-6,11-dihydrodibenz(b,e)oxepin-11-ol
153. 9-cyano-11-aminomethyl-6,11-dihydrodibenz(b,e)oxepin-11-ol
154. 4-cyano-11-methylaminomethyl-6,11-dihydrodibenz(b,e)oxepin-11-ol
155. 7-cyano-11-methylaminomethyl-6,11-dihydrodibenz(b,e)oxepin-11-ol
156. 8-cyano-11-methylaminomethyl-6,11-dihydrodibenz(b,e)-11-ol
157. 9-cyano-11-methylaminomethyl-6,11-dihydrodibenz(b,e)oxepin-11-ol
158. 8-cyano-11-methylaminomethyl-6,11-dihydrodibenz(b,e)thiepin-11-ol
159. 9-cyano-11-methylaminomethyl-6,11-dihydrodibenz(b,e)thiepin-11-ol
160. 4-cyano-11-dimethylaminomethyl-6,11-dihydrodibenz(b,e)oxepin-11-ol
161. 7-cyano-11-dimethylaminomethyl-6,11-dihydrodibenz(b,e)oxepin11-ol
162. 8-cyano-11-dimethylaminomethyl-6,11-dihydrodibenz(b,e)oxepin-11-ol
163. 9-cyano-11-dimethylaminomethyl-6,11-dihydrodibenz(b,e)oxepin-11-ol
164. 4-cyano-11-(2-hydroxyethyl)aminomethyl-6,11-dihydrodibenz(b,e)oxepin-11-ol
165. 7-cyano-11-(2-hydroxyethyl)aminomethyl-6,11-dihydrodibenz(b,e)oxepin-11-ol
166. 8-cyano-11-(2-hydroxyethyl)aminomethyl-6,11-dihydrodibenz(b,e)oxepin-11-ol
167. 9-cyano-11-(2-hydroxyethyl)aminomethyl-6,11-dihydrodibenz(b,e)oxepin-11-ol
168. 4-trifluoromethyl-11-methylaminomethyl-6,11-dihydrodibenz(b,e)oxepin-11-ol
169. 8-trifluoromethyl-11-methylaminomethyl-6,11-dihydrodibenz(b,e)oxepin-11-ol
170. 9-trifluoromethyl-11-methylaminomethyl-6,11-dihydrodibenz(b,e)oxepin-11-ol
171. 4-trifluoromethyl-11-(2-hydroxyethyl)aminomethyl-6,11-dihydrodibenz(b,e)oxepin-11-ol
172. 8-trifluoromethyl-11-(2-hydroxyethyl)aminomethyl-6,11-dihydrodibenz(b,e)oxepin-11-ol
173. 9-trifluoromethyl-11-(2-hydroxyethyl)aminomethyl-6,11-dihydrodibenz(b,e)oxepin-11-ol
174. 2,4-dihydroxy-11-methylaminomethyl-6,11-dihydrodibenz(b,e)oxepin-11-ol
175. 2,4-dimethoxy-11-methylaminomethyl-6,11-dihydrodibenz(b,e)oxepin-11-ol
176. 7,8-dihydroxy-11-methylaminomethyl-6,11-dihydrodibenz(b,e)oxepin-11-ol
177. 7,8-dimethoxy-11-methylaminomethyl-6,11-dihydrodibenz(b,e)oxepin-11-ol
178. 8,9-dihydroxy-11-methylaminomethyl-6,11-dihydrodibenz(b,e)oxepin-11-ol
179. 8,9-dimethoxy-11-methylaminomethyl-6,11-dihydrodibenz(b,e)oxepin-11-ol
180. 4-methylthio-11-methylaminomethyl-6,11-dihydrodibenz(b,e)oxepin-11-ol
181. 8-methylthio-11-methylaminomethyl-6,11-dihydrodibenz(b,e)oxepin-11-ol
182. 9-methylthio-11-methylaminomethyl-6,11-dihydrodibenz(b,e)oxepin-11-ol
183. 4-methylthio-11-dimethylaminomethyl-6,11-dihydrodibenz(b,e)oxepin-11-ol
184. 8-methylthio-11-dimethylaminomethyl-6,11-dihydrodibenz(b,e)oxepin-11-ol
185. 9-methylthio-11-dimethylaminomethyl-6,11-dihydrodibenz(b,e)oxepin-11-ol
186. 4-methylthio-11-(2-hydroxyethyl)aminomethyl-6,11-dihydrodibenz(b,e)oxepin-11-ol
187. 8-methylthio-11-(2-hydroxyethyl)aminomethyl-6,11-dihydrodibenz(b,e)oxepin-11-ol
188. 9-methylthio-11-(2-hydroxyethyl)aminomethyl-6,11-dihydrodibenz(b,e)oxepin-11-ol Example 2

A solution of spiro(6,11-dihydro-dibenz(b,e)oxepin-11,5'-oxazolidone) (2.67 g, 0.01 mole) in 20 ml of anhydrous THF (tetrahydrofuran) is added to a stirred suspension of lithium aluminum hydride (1.5 g) in 15 ml of anhydrous THF under a nitrogen atmosphere. The mixture is refluxed for 18 h and cooled.

Destruction of the excess of lithium aluminum hydride is completed by cautious dropwise addition of 1.5 ml of water followed by 2.3 ml of 15% aqueous sodium hydroxide solution and subsequent addition of 4.5 ml of water. Stirring is continued until a granular white precipitate is formed. Filtration yielded a clear solution. THF is removed under reduced pressure and the residue is dissolved in ether and worked up as in Example 1. The product, 11-methylaminomethyl-6,11-dihydrodibenz(b,e)oxepin-11-ol, hydrochloride, is recrystallized from ethanol:ether, m.p. 152° C. (compound 2:1=compound 1:2).

In essentially the same manner the following compounds are obtained from the corresponding starting materials:

2. 2-chloro-11-(1-amino)ethyl-6,11-dihydrodibenz(b,e)oxepin-11-ol
3. 4-chloro-11(1-amino)ethyl-6,11-dihydrodibenz(b,e)oxepin-11-ol
4. 8-chloro-11-(1-amino)ethyl-6,11-dihydrodibenz(b,e)oxepin-11-ol
5. 9-chloro-11-(1-amino)ethyl-6,11-dihydrodibenz(b,e)oxepin-11-ol
6. 2-chloro-11-(1-methylamino)ethyl-6,11-dihydrodibenz(b,e)oxepin-11-ol
7. 4-chloro-11-(1-methylamino)ethyl-6,11-dihydrodibenz(b,e)oxepin-11-ol
8. 8-chloro-11-(1-methylamino)ethyl-6,11-dihydrodibenz(b,e)oxepin-11-ol
9. 9-chloro-11-(1-methylamino)ethyl-6,11-dihydrodibenz(b,e)oxepin-11-ol
10. 2-chloro-11-(1-(2-hydroxyethyl)amino)ethyl-6,11-dihydrodibenz(b,e)oxepin-11-ol
11. 4-chloro-11-(1-(2-hydroxyethyl)amino)ethyl-6,11-dihydrodibenz(b,e)oxepin-11-ol
12. 8-chloro-11-(1-(2-hydroxyethyl)amino)ethyl-6,11-dihydrodibenz(b,e)oxepin-11-ol
13. 9-chloro-11-(1-(2-hydroxyethyl)amino)ethyl-6,11-dihydrodibenz(b,e)oxepin-11-ol
14. 2-fluoro-11-(1-amino)ethyl-6,11-dihydrodibenz(b,e)oxepin-11-ol
15. 8-fluoro-11-(1-amino)ethyl-6,11-dihydrodibenz(b,e)oxepin-11-ol
16. 9-fluoro-11-(1-amino)ethyl-6,11-dihydrodibenz(b,e)oxepin-11-ol
17. 2-fluoro-11-(1-methylamino)ethyl-6,11-dihydrodibenz(b,e)oxepin-11-ol 18. 8-fluoro-11-(1-methylamino)ethyl-6,11-dihydrodibenz(b,e)oxepin-11-ol
19. 9-fluoro-11-(1-methylamino)ethyl-6,11-dihydrodibenz(b,e)oxepin-11-ol
20. 2-fluoro-11-(1-(2-hydroxyethyl)amino)ethyl-6,11-dihydrodibenz(b,e)oxepin-11-ol
21. 8-fluoro-11-(1-(2-hydroxyethyl)amino)ethyl-6,11-dihydrodibenz(b,e)oxepin-11-ol
22. 9-fluoro-11-(1-(2-hydroxyethyl)amino)ethyl-6,11-dihydrodibenz(b,e)oxepin-11-ol

EXAMPLE 3

A solution of spiro(2-methoxy-6,11-dihydrodibenz(b,e)oxepin-11,5'-N-methyl-oxazolidone) (3.25 g, 0.01 mole), 95% w/w ethanol (200 ml) and 5 g of potassium hydroxide is refluxed for 30 h. The solvent is evaporated under reduced pressure and the residue is dissolved in a mixture of ether and water and worked up as in Example 1. The product, 2-methoxy-11-methylaminomethyl-6,11-dihydrodibenz(b,e)oxepin-11-ol, hydrochloride is recrystallized from ethanol:ether (the same compound as 1:13). M.p. 205° C.

EXAMPLE 4

Sec. butyllithium (1.3 M solution in hexane) (0.77 ml 0.01 mole) is added dropwise under nitrogen at −78° C. to a stirred mixture of 8 ml of trimethylamine and potassium t-butoxide (1.12 g 0.01 mole). The mixture is stirred at 0° C. for 1 h and cooled to −78° C. Thereafter 35 ml of 0.3M solution of lithium bromide in ether is added dropwise. The mixture is stirred 1 h at 0° and cooled to −78° C. and 6,11-dihydro,dibenz(b,e)oxepin-oxepin-11-one (1.68 g, 0.008 mole) in 10 ml of ether is added at −78° C. The reaction mixture is allowed to stay at room temperature over night and poured into ice-water, acidified to pH 3 and extracted twice with ether. The aqueous layer is made alkaline with 2M sodium hydroxide and extracted with ether. The ether extract is washed with water and dried over anhydrous sodium sulphate. The desired product, 11-dimethylaminomethyl-6,11-dihydrodibenz(b,e)oxepin-11-ol, hydrochloride, is isolated and recrystallized from ethanol:ether. M.p. 200 (the same compound as 1:3).

EXAMPLE 5

A solution of N,N-dimethyl-2-methyl-11-hydroxy-6,11-dihydrodibenz(b,e)oxepin-11-carboxamide (2.85 g, 0.01 mole) in 20 ml of anhydrous THF is added to a stirred suspension of lithium aluminium hydride (1.5 g) in 15 ml of anhydrous THF under a nitrogen atmosphere. The mixture is refluxed for 18 h and cooled.

Destruction of the excess of lithium aluminum hydride is completed by cautious dropwise addition of 1.5 ml of water followed by 2.3 ml of 15% aqueous sodium hydroxide solution and subsequent addition of 4.5 ml of water. Stirring is continued until a granular white precipitate is formed. Filtration yields a clear solution. THF is removed under reduced pressure and the residue is dissolved in ether and worked up as in Example 1. The product, 11-methylaminomethyl-6,11-dihydrodibenz(b,e)oxepin-11-ol, hydrochloride, is recrystallized from ethanol:ether. M.p. 237° C. (the same compound as 1:20).

EXAMPLE 6

A mixture of 6,11-dihydrodibenz(b,e)oxepin-11-one (2.10 g, 0.01 mole), zinc iodide (5 mg), and trimethylsilyl cyanide (0.012–0.02 mole) is warmed at 60° C. under a nitrogen atmosphere until the reaction is complete. The excess of trimethylsilylcyanide is removed under reduced pressure and the residue is dissolved in 15 ml of anhydrous THF. The solution is added dropwise to a stirred suspension of lithium aluminium hydride (1 g) in 15 ml of anhydrous THF under a nitrogen atmosphere. The mixture is refluxed for 2 h and cooled.

Destruction of the excess of lithium aluminium hydride is completed by cautious dropwise addition of 1 ml of water followed by dropwise addition of 1.5 ml of 15% aqueous sodium hydroxide solution and subsequent addition of 3 ml of water. Stirring is continued until a granular white precipitate is formed. Filtration yields a clear solution. THF is removed under reduced pressure. The residue is worked up as in Example 2. The product, 11-aminomethyl-6,11-dihydrodibenz(b,e)oxepin-11-ol, is recrystallized from ethanol:ether. M.p. 157° C. (the same compound as 1:1).

EXAMPLE 7

2-Methylthio-11-dimethylaminomethyl-6,11-dihydrodibenz(b,e)oxepin-11-ol, hydrochloride (1.404 g, 4 mmole) is dissolved in 8 ml of trifluoroacetic acid and cooled to −30° C. 8.6 ml of 4M solution of peroxytrifluoro acetic acid in trifluoroacetic acid is added dropwise. The solution is allowed to stay at room temperature. A controlled exothermic reaction starts. After 30 minutes the reaction is complete (the reaction is readily followed by NMR). The solvent is poured into an excess solid sodiumbicarbonate-water mixture and ethyl acetate. The organic extract is washed with 10% sodium bicarbonate and dried over anhydrous sodium sulphate. The desired compound, 2-methylsulfonyl-11-dimethylaminomethyl-6,11-dihydrodibenz(b,e)oxepin-11-ol, hydrochloride, is isolated. M M.p. 247° C. (compound 7:1)

In essentially the same manner the following compounds are obtained from the corresponding starting materials:

2. 4-methylsulfinyl-11-methylaminomethyl-6,11-dihydrodibenz(b,e)oxepin-11-ol
3. 8-methylsulfinyl-11-methylaminomethyl-6,11-dihydrodibenz(b,e)oxepin-11-ol
4. 9-methylsulfinyl-11-methylaminomethyl-6,11-dihydrodibenz(b,e)oxepin-11-ol
5. 4-methylsulfonyl-11-methylaminomethyl-6,11-dihydrodibenz(b,e)oxepin-11-ol
6. 8-methylsulfonyl-11-methylaminomethyl-6,11-dihydrodibenz(b,e)oxepin-11-ol
7. 9-methylsulfonyl-11-methylaminomethyl-6,11-dihydrodibenz(b,e)oxepin-11-ol

EXAMPLE 8

A solution of 11-acetamidomethyl-6,11-dihydrodibenz(b,e)oxepin-11-ol (2.71 g, 0.01 mole) in 20 ml of anhydrous THF is added to a stirred suspension of lithium aluminium hydride (1.5 g) in 15 ml of anhydrous THF under a nitrogen atmosphere. The mixture is refluxed for 18 h and cooled.

Destruction of the excess of lithium aluminum hydride is completed by cautious dropwise addition of 1.5 ml of water followed by 2.3 ml of aqueous sodium hydroxide solution and subsequent addition of 4.5 ml of water. Stirring is continued until a granular white precipitate is formed. Filtration yields a clear solution. THF is removed under reduced pressure and the residue is dissolved in ether and worked up as in Example 1.

The product, 11-ethylaminomethyl-6,11-dihydrodibenz(b,e)oxepin-11-ol, hydrochloride is recrystallized from ethanol:ether. M.p. 181° C. (the same compound as 1:4).

EXAMPLE 9

A stirred mixture of 11-hydroxy-6,11-dihydrodibenz(b,e)oxepin-11-ol aldehyde (3 g), 10 ml of a 40 wt % solution of methyl amine in methanol, 35 ml of ethanol and 5 wt % Pd/active charcoal catalyst (0.5 g) is hydrogenated at 30° C. and 20 atm. until slightly more than the stoichiometric amount of hydrogen is absorbed and then filtered.

The solution is concentrated. The residue is poured into 100 ml of water and worked up as in Example 1.

The product, 11-methylaminomethyl-6,11-dihydrodibenz(b,e)oxepin-11-ol, hydrochloride is recrystallized from ethanol:ether. M.p. 152° C. (the same compound as 1:2).

EXAMPLE 10

The following example illustrates resolution of a racemate according to the invention:

2-Chloro-11-dimethylaminomethyl-6,11-dihydrodibenz(b,e)oxepin-11-ol (37.38 g, 0.123 mole) and di-0,0'-p-toluoyl-L-tartaric acid (49.7 g, 0.123 mole) are mixed in and the product crystallized from 140 ml of 90% ethanol. The product, 44 g, is recrystallized twice from 90% ethanol and converted via base to the hydrochloride of (−)-2-chloro-11-dimethylamino-6,11-dihydrodibenz(b,e)oxepin-11-ol. Yield 16.7 g. M.p. 217.2° C. $(\alpha)_D^{25,1} = -147.3°$ (C=1% in ethanol)

The mother liquor from the first crystallization is concentrated to almost dryness on a rotary evaporator. The residue is treated with 5M ammonium hydroxide and extracted with ether. The ether layer is evaporated (17.8 g, 0.058 mole) and crystallized with di-0,0'-p-toluoyl-D-tartaric acid (23.7 g, 0.058 mole) from 130 ml 90% ethanol. The product (36.3 g) was converted via base to the hydrochloride of (+)-2-chloro-6,11-dihydrodibenz(b,e)oxepin-11-ol. Yield 16.5 g. M.p. 217.2° C. $(\alpha)_D^{24,1} = +145.4°$ (C=1% in ethanol).

The following racemic compounds are resolved:
8-fluoro-11-methylaminomethyl-6,11-dihydrodibenz(b,e)oxepin-11-ol
9-fluoro-11-methylaminomethyl-6,11-dihydrodibenz(b,e)oxepin-11-ol
8-chloro-11-methylaminomethyl-6,11-dihydrodibenz(b,e)oxepin-11-ol
9-chloro-11-methylaminomethyl-6,11-dihydrodibenz(b,e)oxepin-11-ol
8-chloro-11-dimethylaminomethyl-6,11-dihydrodibenz(b,e)oxepin-11-ol
9-chloro-11-dimethylaminomethyl-6,11-dihydrodibenz(b,e)oxepin-11-ol
8-chloro-11-(2-hydroxyethyl)aminomethyl-6,11-dihydrodibenz(b,e)oxepin-11ol
9-chloro-11-(2-hydroxyethyl)aminomethyl-6,11-dihydrodibenz(b,e)oxepin-11-ol,
8-cyano-11-methylaminomethyl-6,11-dihydrodibenz(b,e)oxepin-11-ol
9-cyano-11-methylaminomethyl-6,11-dihydrodibenz(b,e)oxepin-11-ol
9-cyano-11-dimethylaminomethyl-6,11-dihydrodibenz(b,e)oxepin-11-ol
8-cyano-11-(2-hydroxyethyl)aminomethyl-6,11-dihydrodibenz(b,e)oxepin-11-ol
9-trifluoromethyl-11-methylaminomethyl-6,11-dihydrodibenz(b,e)oxepin-11-ol
8-trifluoromethyl-11-(2-hydroxyethyl)aminomethyl-6,11-dihydrodibenz(b,e)oxepin-11-ol
9-chloro-11-(1-amino)ethyl-6,11-dihydrodibenz(b,e)oxepin-11-ol
8-chloro-11-(1-methylamino)ethyl-6,11-dihydrodibenz(b,e)oxepin-11-ol

EXAMPLE 11

| Manufacturing process for tablets of 20 mg Model batch of 1000 tablets | | |
|---|---|---|
| I | Active Compound, mesh+ 70 | 20 g |
|  | Lactosum, Ph. Nord. | 210 g |
|  | Amylum maidis, Ph. Nord. | 75 g |
| II | Kollidon 25, B.A.S.F. | 3.5 g |
|  | Aqua purificata | q.s. |
| III | Talcum, Ph. Nord. | 15 g |
|  | Magnesii stearas, Ph. Nord. | 1.5 g |
| Weight of 1000 tablets | | 325 g |
| Weight of 1 tablet: 325 mg | | |

+The mesh standard is according to the international system of code DIN 4189/1968.
Punch: 10.5 mm round, flat, scored, bevel-edged Mix the screened substances I thoroughly and then moisten with II, whereupon the mixture is granulated through a stainless sieve No. 10 (mesh 25). Dry the granulate in an oven at a maximum temperature of 40° C. then repeat sieving through sieve No. 10. Add the substances under III and mix thoroughly. Punch tablets with a gross weight of about 325 mg.

EXAMPLE 12

| Suspension for injection 20 mg/ml | |
|---|---|
| Active Compound, mesh 100 | 20 mg |
| Sodium Chloride | 8 mg |
| Carboxy methylcellulose | 1 mg |
| Benzyl alcohol | 1 mg |
| Distilled water to make | 1 ml |

EXAMPLE 13

| Oral suspension 5 mg/ml | |
|---|---|
| Active Compound, mesh 100 | 20 mg |
| Sorbitol | 600 mg |
| Flavoring compound | q.s. |
| Colour | q.s. |
| Water to make | 1 ml |

EXAMPLE 14

| Suppositoria of 25 mg | |
|---|---|
| Active Compound | 25 mg |
| Cocoa butter | q.s. |

EXAMPLE 15

| Ointment 2% | | |
|---|---|---|
| Active compound | 2 g | g |
| Triethanolamine | 1 g | g |
| Glycerol | 7 g | g |
| Cetanol | 2.5 g | g |
| Lanolin | 2.5 g | g |

| -continued | | |
|---|---|---|
| Ointment 2% | | |
| Stearic acid | 20 g | g |
| Sorbitan monooleate | 0.5 g | g |
| Sodium hydroxide | 0.2 g | g |
| Methyl paraben | 0.3 g | g |
| Propyl paraben | 0.1 g | g |
| Ethanol | 0.9 g | |
| Water to make | 100 g | g |

EXAMPLE 16

| Capsules of 10 mg | | |
|---|---|---|
| Active compound | 10 mg | mg |
| Magnesium stearate | 2 mg | mg |
| Talcum | 188 mg | |

The substances are mixed and filled in capsules. EXAMPLE 17

| 20 mg sterile powder to be dissolved in water for injection | | |
|---|---|---|
| Watersoluble Active Compound | 10 mg | mg |
| Sodium chloride | 4 mg | mg |
| Methyl paraben | 0.7 mg | mg |
| Propyl paraben | 0.3 mg | mg |

The substances are dissolved in distilled water.
The solution is dispensed in vials and freeze-dried.

EXAMPLE 18

| Injectable solution 20 mg/ml | | |
|---|---|---|
| Watersoluble Active Compound | 20 mg | |
| Ascorbic acid | 1 mg | |
| Sodium bisulfite | 1 mg | |
| Sodium chloride | 6 mg | |
| Methyl paraben | 0.7 mg | |
| Propyl paraben | 0.3 mg | |
| Distilled water to make | 1 ml | |

In the foregoing Examples 11–18 relating to compositions the Active Compounds are those covered by the general formula I above or their addition salts with pharmaceutically acceptable inorganic or organic acids. Watersoluble Active Compounds are such addition salts or salts with a pharmaceutically acceptable inorganic or organic cation.

Also, it is to be noted that two or more Active Compounds of the invention may be used in combination in the compositions illustrated, and also, if desired, in combination with other pharmacologically active agents.

| REFERENCES: | | |
|---|---|---|
| 1. A. S. Rao, et al | Tetrahedron 39 (1983), 2323 and references cited therein | |
| 2. G. Schroeter | Chem. Zentr. 81, I, 1470 (1910) | |
| 3. H. Ahlbrecht, et al | Tetrahedron Letters 25 (1984), 1353 | |
| 4. J. P. Quintard, et al | Syntheses 1984, 495 | |
| 5. A. Rosowsky V. J. Traynelis | Weissberger: Heterocyclic compounds Vol. 26 (1972) and references cited therein | |
| 6. P. Beak, et al | Chemical Reviews 78 (1978), 275 Chemical Reviews 84 (1984), 471 and references cited therein | |
| 7. W. C. Groutas, et al | Synthesis 1980, 861 and references cited therein | |
| 8. B. M. Trost, et al | Tetrahedron Letters 22 (1981), 1287 | |
| 9. C. G. Venier, et al | J. Org. Chem. 47 (1982), 3773 | |

| REFERENCES: | | |
|---|---|---|
| 10. J. Jacques, et al | Enantiomers, Racemates and Resolutions John Wileys & Sons, 1981, 256 | |
| 11. D. S. Watt, et al | J. Org. Chem. 49 (1984), 1378 | |
| 12. V. Reutrakul | Chem. Lett. 1980, 71 | |

What we claim is:

1. A dibenz(b,e)oxepin or dibenz(b,e)thiepin compound selected from the group consisting of those having the formula:

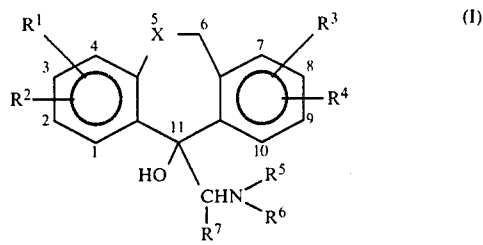

wherein
X is O or S,
$R^1$, $R^2$, $R^3$ and $R^4$ are the same or different and are each selected from the group consisting of hydrogen, lower alkyl, lower alkenyl, lower alkynyl, lower cycloalkyl, lower alkoxy, lower alkylthio, lower alkylsulphinyl, lower alkylsulphonyl, halogen, trifluoromethyl, trifluoromethylthio, lower dialkylsulphonamido, nitro, hydroxy, cyano, carbamyl, carboxy, lower alkoxycarbonyl, amino, N-lower alkylamino, N,N-dilower alkylamino, lower acylamido, lower alkanesulfonamido and lower acyl; and, when on adjacent carbon atoms at the positions 2 and 3 and/or 8 and 9, two of the substituents $R^1$ and $R^2$ or $R^3$ and $R^4$ taken together may form a methylenedioxy group;

$R^5$ and $R^6$ are the same or different and are selected from the group consisting of hydrogen, lower alkyl, lower alkenyl, lower alkynyl, lower cycloalkyl, aralkyl, lower hydroxyalkyl, lower aminoalkyl, lower alkylaminoalkyl, lower dialkylaminoalkyl, lower alkoxyalkyl and, taken together with the nitrogen atom, a 5- or 6-membered ring selected from pyrrolidine, piperidine, morpholine, piperazine, N-lower alkyl or N-hydroxy lower alkyl substituted rings such as N-alkyl piperazine or N-hydroxyalkylpiperazine or the like;

and $R^7$ is hydrogen or lower alkyl;
and enantiomers thereof;
and pharmaceutically acceptable acid addition salts of any of the foregoing.

2. Compounds according to claim 1, characterized in that $R^1$, $R^2$, $R^3$ and $R^4$ are the same or different and are selected from the group consisting of hydrogen, lower alkyl, lower alkoxy, hydroxy, halogen, trifluoromethyl, cyano, carboxy, lower alkoxycarbonyl, amino, lower alkylamino, N,N-dilower alkylamino, lower acylamido, lower alkanesulfonamido.

3. Compound according to claim 1, characterized in that $R^1$, $R^2$, $R^3$ and $R^4$ are the same or different and selected from the group consisting of hydrogen, methyl, methoxy, hydroxy, chloro, fluoro, bromo, trifluoromethyl, cyano, carboxy, methoxycarbonyl, amino, methylamino, dimethylamino, formamido, acetamido, methanesulfonamido, trifluormethanesulfonamido.

4. Compound according to any of the claims 1–3, characterized in that $R^5$ and $R^6$ are the same or different and selected from the group consisting of hydrogen, methyl, ethyl and hydroxyethyl.

5. Compound according to claim 1 selected from the group consisting of:

2-chloro-11-dimethylaminomethyl-6,11-dihydrodibenz(b,e)oxepin-11-ol 9-chloro-11-dimethylaminomethyl-6,11-dihydrodibenz(b,e)oxepin-11-ol 2,9-dichloro-11-dimethylaminomethyl-6,11-dihydrodibenz(b,e)oxepin-11-ol 9-chloro-11-methylaminomethyl-6,11-dihydrodibenz(b,e)thiepin-11-ol 8-chloro-11-dimethylaminomethyl-6,11-dihydrodibenz(b,e)thiepin-11-ol 8-fluoro-11-methylaminomethyl-6,11-dihydrodibenz(b,e)oxepin-11-ol 9-fluoro-11-dimethylaminomethyl-6,11-dihydrodibenz(b,e)oxepin-11-ol 8-chloro-11-methylaminomethyl-6,11-dihydrodibenz(b,e)oxepin-11-ol 9-chloro-11-methylaminomethyl-6,11-dihydrodibenz(b,e)oxepin-11-ol 4-chloro-11-dimethylaminomethyl-6,11-dihydrodibenz(b,e)oxepin-11-ol 8-chloro-11-dimethylaminomethyl-6,11-dihydrodibenz(b,e)oxepin-11-ol 9-chloro-11-dimethylaminomethyl-6,11-dihydrodibenz(b,e)oxepin-11-ol 8-chloro-11-(2-hydroxyethyl)aminomethyl-6,11-dihydrodibenz(b,e)oxepin-11-ol 9-chloro-11-(2-hydroxyethyl)aminomethyl-6,11-dihydrodibenz(b,e)oxepin-11-ol 9-cyano-11-methylaminomethyl-6,11-dihydrodibenz(b,e)oxepin-11-ol 8-cyano-11-(2-hydroxyethyl)aminomethyl-6,11-dihydrodibenz(b,e)oxepin-11-ol 9-trifluoromethyl-11-methylaminomethyl-6,11-dihydrodibenz(b,e)oxepin 11-ol 7,8-dihydroxy-11-methylaminomethyl-6,11-dihydrodibenz(b,e)oxepin-11-ol 2-chloro-11-(1-amino)ethyl-6,11-dihydrodibenz(b,e)oxepin-11-ol 8-chloro-11-(1-amino)ethyl-6,11-dihydrodibenz(b,e)oxepin-11-ol 9-chloro-11-(1-amino)ethyl-6,11-dihydordibenz(b,e)oxepin-11-ol 8-fluoro-11-(1-methylamino)ethyl-6,11-dihydrodibenz(b,e)oxepin-11-ol.

6. Pharmaceutical composition useful for the amelioration of urinary incontinence containing as active ingredient one or more compound of claim 1 in an amount effective for such purpose together with a pharmaceutically acceptable carrier therefor.

7. A method of treating a living body affiliated with a condition of urinary incontinence which comprises the step of administering to said living body a compound of claim 1 in an amount effective for amelioration of such condition.

* * * * *